United States Patent [19]
Puy

[11] Patent Number: 5,945,552
[45] Date of Patent: Aug. 31, 1999

[54] FLUORINATED VINYL OXIRANES

[75] Inventor: Michael Van Der Puy, Amherst, N.Y.

[73] Assignee: AlliedSignal Inc., Morristown, N.J.

[21] Appl. No.: 08/975,310

[22] Filed: Nov. 21, 1997

[51] Int. Cl.$^6$ .................................................. C07D 303/08
[52] U.S. Cl. .......................................................... 549/563
[58] Field of Search ............................................. 549/563

[56] References Cited

U.S. PATENT DOCUMENTS

| | | | |
|---|---|---|---|
| 5,328,971 | 7/1994 | Blevins | 526/209 |
| 5,481,050 | 1/1996 | Van Der Puy et al. | 570/135 |

OTHER PUBLICATIONS

M. Van Der Puy/Journal of Fluorine Chemistry 81 (1997) 187–191.

Chan et al., Organometallic Reactions in Aqueous Medium, Organometallic, vol. 9, No. 10, 1990, pp. 2649–2650.

Marshall, Additions of Organocopper Reagents to Vinyloxiranes, Chemical Reviews, 1989, vol. 89, No. 7, pp. 1503–1511.

*Primary Examiner*—Ba K. Trinh
*Attorney, Agent, or Firm*—Jay P. Friedenson; Colleen D. Szuch

[57] ABSTRACT

A compound having the formula:

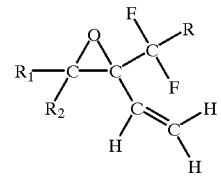

wherein:
R is fluorine, hydrogen, an unsubstituted or substituted aliphatic or unsubstituted or substituted aromatic radical;
$R_1$ is an unsubstituted or substituted aliphatic radical, or unsubstituted or substituted aromatic radical; and
$R_2$ is hydrogen, an unsubstituted or substituted aliphatic radical, or unsubstituted or substituted aromatic radical.

8 Claims, No Drawings

FLUORINATED VINYL OXIRANES

FIELD OF THE INVENTION

The present invention relates to useful fluorinated materials. More specifically, this invention relates to a family of fluorinated vinyl oxirane compounds, a method of preparing them, their uses, and the products resulting from their use.

It is well known that incorporating fluorine into organic compounds can beneficially alter their characteristics. For example, fluorine is known to improve a material's surface properties, such as gas/moisture permeability and surface tension. Such characteristics are important for polymers used in finishes, coatings, films, and the like. Additionally, fluorine is known to improve chemical properties, such as hydrolytic stability and potency. Improving chemical properties is especially important in bioactive organic compounds where minimizing dosage is a primary concern. Consequently, the incorporation of fluorinated groups, particularly trifluoromethyl groups, is common in the preparation of biomedical materials. (See, for example, A Becker, Inventory of Industrial Fluorobiochemicals (Editions Eyrolles (1996)). Therefore, fluorinated organic compounds are desirable for many applications.

The effectiveness of fluorination, however, depends significantly upon the placement of the fluorine in the compound. For example, in bioactive compounds, relatively few fluorine atoms per molecule, typically from about 1 to about 3, are required to impart the desired effect, provided that the fluorine atoms are located at key positions in the molecule. Since the effectiveness of fluorination is often critically dependent on placement, the industry continually seeks new and effective means for selectively fluorinating organic compounds.

Therefore, the selective incorporation of fluorine at specific sites in organic molecules, particularly complex organic molecules, has created a need for new fluorochemical reagents and synthesis methodologies. The present invention fulfills this need among others.

DESCRIPTION OF THE INVENTION AND PREFERRED EMBODIMENTS

The present invention provides a family of fluorinated vinyl oxirane compounds which are useful as intermediates for making other compounds, including polymeric compounds, that include fluorine atoms. The vinyl oxirane compounds of the present invention combine the beneficial properties of fluorine with the reactive properties of vinyl oxirane compounds. The reactivity of vinyl oxirane compounds arises from their dual functionality—a terminal vinyl group and an epoxide ring. Either independently or in concert, these functional groups enable vinyl oxirane compounds to react readily with a diverse array of organic compounds. The incorporation of one or more fluorine atoms into a vinyl oxirane compound therefore results in a fluorinated compound which in turn can be used for introducing fluorine atoms into other materials including, for example, commercially-significant materials such as bioactives which are used for biomedical or agricultural applications and polymers which are used for finishes and coatings.

One aspect of the present invention comprises a fluorinated compound of the following general formula:

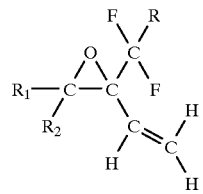

(1)

wherein:
R is a fluorine, hydrogen, an unsubstituted or substituted aliphatic or unsubstituted or substituted aromatic radical;
$R_1$ is an unsubstituted or substituted aliphatic radical, or unsubstituted or substituted aromatic radical; and
$R_2$ is a hydrogen, an unsubstituted or substituted aliphatic radical, or unsubstituted or substituted aromatic radical.

Another aspect of the invention is the provision of a process for preparing a fluorinated vinyl oxirane compound, preferably of Formula (1). In a preferred embodiment, the process comprises: (a) converting an allylic halide having at least one fluorinated group to a fluorinated homoallylic alcohol using a metallic reagent; and (b) converting the fluorinated homoallylic alcohol to the fluorinated vinyl oxirane using a base.

Yet another aspect of the present invention relates to uses for a fluorinated vinyl oxirane compound, preferably of Formula (1). The use may comprise any conventional use for a vinyl oxirane compound. In preferred embodiments, a fluorinated vinyl oxirane compound is reacted with a carbon nucleophile to produce a fluorinated allylic alcohol, or with one or more unsaturated monomers to produce a fluorinated polymer having epoxide functionality which is available for other reactions, for example, cross linking, if desired.

Still another aspect of the present invention are the fluorinated organic compounds produced by reacting the fluorinated vinyl oxirane compound as mentioned above.

Various aspects of the invention are related to the fluorinated vinyl oxirane compound of Formula (1). In that formula, R can be fluorine, hydrogen, an unsubstituted or substituted aliphatic radical, or an unsubstituted or substituted aromatic radical. Preferably, R is fluorine, hydrogen, an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical. More preferably, R is fluorine, hydrogen, an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl or an unsubstituted or substituted $C_7$–$C_{11}$ aralkyl. Examples of substitution groups include fluorine, $C_1$–$C_6$ alkyls, $C_1$–$C_6$ halogenated alkyls, $C_6$–$C_{15}$ aryls, $C_1$–$C_6$ alkoxys, and cyanos.

R as a $C_1$–$C_{10}$ alkyl may be straight chain or branched, for example, methyl, ethyl, propyl, isopropyl, butyl, isobutyl, pentyl, isopentyl, hexyl, heptyl, octyl, and ethylhexyl. In a more preferred class of alkyls, R is a perfluorinated $C_1$–$C_6$ alkyl, in the most preferred class, R is trifluoromethyl.

R as a $C_3$–$C_8$ cycloalkyl may be, for example, cyclopropyl, cyclobutyl, cyclopentyl, methylcyclopentyl, cyclohexyl, methylcyclohexyl, dimethylcyclohexyl, cycloheptyl or cyclooctyl, and, preferably, cyclohexyl.

R as a 3–6 ring member heterocyclic radical may have any known heterocylic atom such as N, O, and S. Suitable fluorinated heterocycles include, for example, pyridine, pyran, thiophan, pyrrole, furan, and thiophen.

R as a $C_6$–$C_{15}$ aryl may be, for example, phenyl, -o-tolyl, -m-tolyl, -p-tolyl, -o-xylyl, -m-xylyl, -p-xylyl, -alpha-naphthyl or -beta-naphthyl. In a preferred class of aryl compounds, R is a $C_6$–$C_8$ aryl or a $C_{12}$–$C_{14}$ aryl, especially perfluoroaryl, such as pentafluorophenyl and nonofluoronaphthyl.

R as a fluorinated $C_7$–$C_{13}$ aralkyl may be, for example, benzyl, methylbenzyl, methoxybenzyl, diphenylmethyl, phenylethyl, or phenylpropyl. In a preferred class of aralkyl compounds, R is a $C_7$–$C_9$ aralkyl, especially pentafluorobenzyl.

In a still more preferred embodiment, R is fluorine or a polyhalogenated $C_1$–$C_3$ alkyl such as $CF_3$, $CF_2Cl$, $CF_2H$, $ClCF_2$, and $ClCF_2CF_2$.

In Formula (1), $R_1$ can be an unsubstituted or substituted aliphatic radical, or an unsubstituted or substituted aromatic radical. Preferably, $R_1$ is an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical. More preferably, $R_1$ is an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl, or an unsubstituted or substituted $C_7$–$C_{11}$ aralkyl. Examples of substitution groups include fluorine, $C_1$–$C_6$ alkyls, $C_1$–$C_6$ halogenated alkyls, $C_6$–$C_{15}$ aryls, $C_1$–$C_6$ alkoxys, nitros, aminos (primary and secondary), amidos, and cyanos.

$R_1$ as a $C_1$–$C_{10}$ alkyl may be a straight chain or branched molecule, for example, methyl, ethyl, n-propyl, isopropyl, n-butyl, isobutyl, tert-butyl, n-pentyl, neopentyl, n-hexyl, n-heptyl, n-octyl, or 2-ethylhexyl. Additionally, any of these groups may substituted with methoxy, ethoxy, n-propoxy, isopropoxy, n-butoxy, methanesulphonyl, cyano, bromine, chlorine or fluorine, among others, to form such substituted alkyl groups as methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-cyanoethyl, 2-fluoroethyl, 2,2,2-trifluoroethyl, trichloromethyl, 2-chloroethyl, 2-(chloromethyl)ethyl, 2,2, 2-trichloroethyl, 2-chloro-n-propyl or 3-chloro-n-butyl. In a preferred class of alkyls, $R_1$ is an $C_1$–$C_6$ alkyl, which may be substituted by cyano, halogen or $C_1$–$C_4$ alkoxy, especially methyl, ethyl, n-butyl, 2-cyanoethyl, 1-(chloromethyl) ethyl or 2-methoxyethyl. In another preferred class of alkyls, $R_1$ is a branched alkyl, preferably a $C_2$–$C_6$ branched alkyl, especially isobutyl.

$R_1$ as a $C_3$–$C_8$ cycloalkyl may be, for example, cyclopropyl, cyclobutyl, cyclopentyl, methylcyclopentyl, cyclohexyl, methylcyclohexyl, dimethylcyclohexyl, cycloheptyl or cyclooctyl, preferably cyclohexyl. Any of these groups may be substituted with, for example, methoxy, ethoxy, n-propoxy, isopropoxy, n-butoxy, cyano, chlorine or fluorine. In a preferred class of cycloalkyl, $R_1$ is a $C_5$–$C_7$ cycloalkyl, and, more preferably, cyclohexyl.

$R_1$ as a 3–6 ring member heterocyclic radical may include any known heterocylic atom such as N, O, and S. Suitable heterocycles include, for example, pyridine, pyran, thiophan, pyrrole, furan, and thiophen.

$R_1$ as a $C_6$–$C_{15}$ aryl may be, for example, phenyl, o-tolyl, m-tolyl, p-tolyl, o-xylyl, m-xylyl, p-xylyl, alpha-naphthyl or beta-naphthyl. Any of these groups may be substituted with, for example, halogen, $C_1$–$C_4$ alkoxy or nitro. In a preferred class of aryls, $R_1$ is $C_6$–$C_8$ aryl or $C_{12}$–$C_{14}$ aryl, and, more preferably, phenyl or naphthyl.

$R_1$ as $C_7$–$C_{13}$ aralkyl may be, for example, benzyl, 4-methylbenzyl, o-methoxybenzyl, p-methoxybenzyl, diphenylmethyl, 2-phenylethyl, 2-phenylpropyl or 3-phenylpropyl, preferably $C_7$–$C_9$ aralkyl, especially benzyl.

In a still more preferred embodiment, $R_1$ is an aryl group, especially a substituted or unsubstituted phenyl group.

$R_2$ is similar to $R_1$ with regard to the preferred and more preferred groups described above, however, $R_2$ may also be a hydrogen radical and the still more preferred embodiment of $R_2$ is hydrogen.

In Table 1 below, a preferred selection of group combinations for Formula (1) is presented. It should be noted that the combinations listed are for illustrative purposes and other combinations of R, $R_1$, and $R_2$ are well within the scope of the invention.

TABLE 1

Preferred Combinations of R, $R_1$, and $R_2$

| Combination | R | $R_1$ | $R_2$ |
|---|---|---|---|
| 1 | F | phenyl | H |
| 2 | F | isopropyl | H |
| 3 | F | n-butyl | H |
| 4 | F | phenyl | phenyl |
| 5 | F | 2-fluoro-4-chlorophenyl | H |
| 6 | $CF_3$ | phenyl | H |
| 7 | $CF_3$ | t-butyl | H |
| 8 | $CF_3$ | 2-thienyl | H |
| 9 | $CF_3$ | 2-furanyl | H |
| 10 | $ClCF_2$ | phenyl | H |
| 11 | $ClCF_2$ | t-butyl | H |
| 12 | $ClCF_2$ | methyl | methyl |
| 13 | $ClCF_2CF_2CF_2$ | phenyl | H |
| 14 | $ClCF_2CF_2CF_2$ | isopropyl | H |
| 15 | $ClCF_2CF_2CF_2$ | 4-$CH_3$-phenyl | H |
| 16 | $HCF_2$ | phenyl | H |
| 17 | $HCF_2$ | ethyl | H |
| 18 | $HCF_2$ | sec-butyl | H |
| 19 | $HCF_2$ | 3-fluorophenyl | H |
| 20 | H | 2-naphthyl | H |

The synthesis of fluorinated vinyl oxirane compounds of Forumla (1) is novel. In a preferred embodiment, the synthesis begins with a starting material comprising an allylic halide substituted with at least one fluorinated group. A preferred family of such starting materials has the following formula:

$$RCF_2CX_{2-z}CHCH_2X_z \qquad (2)$$

wherein X is a halogen other than fluorine and z is 0 or 1. In a more preferred embodiment, the interior halogen in Formula (2) is chlorine resulting in the following formula:

$$RCF_2CCl_{2-z}CHCH_2X_z \qquad (3)$$

One approach to synthesizing this compound when X=Cl and z=0 or 1 to form $RCF_2CCl=CHCH_2Cl$ or $RCF_2CCl_2CH=CH_2$, respectively, is taught, for example, in U.S. Pat. No. 5,481,050 and M. Van Der Puy, 81 J. FLUORINE CHEM. 187 (1997). Another method of synthesizing the compound of Formula (3) when z=1 and X=Br or I to from $RCF_2CCl=CHCH_2Br$ or $RCF_2CCl=CHCH_2I$, respectively, is provided in U.S. Pat. No. 5,654,473. An even more preferred embodiment of the invention starts with an allylic halide of Formula (3) wherein z=1 and X is either Br or I.

The fluorinated vinyl oxiranes are made in two steps from the starting material. First, the starting material is converted to a fluorinated homoallylic alcohol having a terminal vinyl group. Second, the fluorinated homoallylic alcohol is converted to a fluorinated vinyl oxirane.

In the first step, the conversion is performed preferably by producing an organometallic reagent of the starting material and then reacting it with a carbonyl compound to form a fluorinated homoallylic alcohol. The organometallic reagent can be produced from the starting using conventional techniques.

In a preferred embodiment, the starting material of Formula (2) is reacted with a transitional metal in a non-reactive solvent to form a fluorinated organometallic compound having the following formula:

$$RCF_2CX(MX)CH=CH_2 \quad (4)$$

wherein M is a transition metal. In a more preferred embodiment, wherein the allylic halide of Formula (3) is used, the resulting fluorinated organometallic compound has the following formula:

$$RCF_2CCl(MX)CH=CH_2 \quad (5)$$

A metal should be used such that the resulting organometallic compound is not so reactive that it is unstable and consequently reacts too readily with the other reaction materials before reacting with the carbonyl compound. For example, a Grignard reagent tends to be too reactive. The transition metal is preferably selected from zinc, cadmium, or copper, and, most preferably, the metal is zinc. The solvent may be water or an organic solvent. Preferably, the solvent is an organic solvent, and, more preferably, it is an amide solvent, such as dimethylformamide or dimethylacetamide, or an ether solvent, such as dioxane, dimethoxyethane, or tetrahydrofuran (THF). In cases where the starting material is $CF_3CC_{12}CH=CE_2$ or $CF_3CCl=CHCH_2Cl$, which tends to be less reactive than compounds having terminal bromine or iodine, it is preferable to use amide solvents, most preferably, dimethylformamide.

In light of this disclosure, someone skilled in the art can readily determine and optimize the reaction conditions for preparing the organometallic reactant without undue experimentation. Typically, the reaction occurs at temperatures of about 0 to about 100° C., and preferably at about 20 to about 50° C. For example, the reaction of the starting material of Formula (3) with a zinc and THF occurs at room temperature. After an induction period, the reaction becomes moderately exothermic, making temperature control with a cooling bath desirable, especially for larger scale preparations.

Next, the fluorinated organometallic reagent of formula (4) is reacted with a carbonyl compound to form a fluorinated homoallylic alcohol having the following formula:

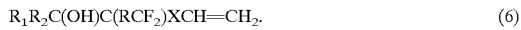

$$R_1R_2C(OH)C(RCF_2)XCH=CH_2. \quad (6)$$

The $R_1$ and $R_2$ groups of this formula are the same as those in Formula (1) and are introduced to this compound via the carbonyl compound. In a more preferred embodiment, a fluorinated organometallic reagent of Formula (5) is reacted with an aldehyde or a ketone to form a fluorinated homoallylic alcohol having the following formula:

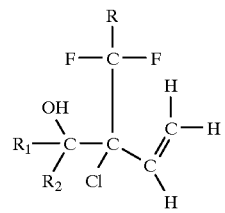

(7)

With an aldehyde ($R_1R_2CO$), $R_2$ is a hydrogen radical, and with a ketone ($R_1COR_2$) neither $R_1$ or $R_2$ is a hydrogen radical. The most preferred carbonyl compound is an aldehyde.

Since the fluorinated organometallic reagent tends to be highly reactive, it is preferred to introduce the carbonyl compound as soon as possible to limit unwanted reactions. Therefore, in the preferred embodiment, the carbonyl compound is present in the metallic solution described above so that it reacts immediately with the reagent before the latter has an opportunity to react with the other reaction materials such as the starting material. In light of this disclosure, someone skilled in the art can readily determine and optimize the reaction conditions for preparing a fluorinated homoallylic alcohol without undue experimentation.

The alcohol product of the first step is generally a high-boiling liquid which is readily recovered by distillation. Nevertheless, the crude product may be sufficiently pure to use in the second step without further purification.

In the second step, the alcohol prepared in the first step is treated with a base to form the oxirane. For example, when the alcohol of Formula (7) is used, introducing at least a molar equivalent of base removes HCl from the compound causing an oxirane to form. The base may be organic or inorganic. Preferred inorganic bases include, for example, aqueous NaOH, KOH, or $NaCO_3$ solutions, and preferred organic bases include, for example, amines and alkoxides.

When an aqueous base is used, the reaction mixture of the fluorinated allylic alcohol and base tends be two phases since the alcohol is immiscible in water. Consequently, it is preferable to undertake steps to facilitate mixing. One common approach is to heat the reaction mixture. Although effective in increasing miscibility, heating tends to increase the formation of unwanted by-products. Therefore, other techniques for promoting mixing are preferred. Examples of such techniques include, for example, the use of phase-transfer catalysts, such as tetraalkylammonium salts ("quats") to allow the reaction to be conducted at the lower end of the temperature range. Alternatively, a co-solvent may be used, such as methanol, acetonitrile, dimethylsulfoxide, dimethylformamide, and the like.

In light of this disclosure, someone skilled in the art can readily determine and optimize the reaction conditions for preparing the fluorinated vinyl oxirane compound without undue experimentation. Generally, reaction temperatures generally range from about 25 to about 150° C., and reaction times range from a few minutes to several hours.

According to the present invention, a family of fluorinated vinyl oxirane compounds is provided which can be used to introduce fluorinated groups into organic molecules. The fluorinated vinyl oxirane compounds of the present invention can be used in a similar fashion as any conventional vinyl oxirane compound is used. Vinyl oxiranes compounds are particularly useful in the preparation of bioactive allylic alcohols of diverse structure (see J. A. Marshall, *Chemical Reviews*, 89 (1989) 1503). Other uses of vinyl oxiranes, include, for example, wash resistant finishes for fabrics (CA 115:P10793t), water proofing (CA 113:P99720w and 101:P56025h), and in various polymers (CA 108:P151166h, 96:P53289q, 99:P89595n), since they can be copolymerized with e.g. ethylene. Still other applications of the compound of the present invention will be apparent to someone skilled in the art in light of this disclosure.

EXAMPLES

The following examples are illustrative of the practice of the present invention.

Example 1

This example illustrates the preparation of 2-tifluoromethyl-2-vinyl-3-phenyl oxirane from $CF_3CCl=CHCH_2I$.

Zinc powder (10.2 g) was activated by treatment with 20 ml 1N HCl, followed by washing with 25 ml ethanol and 2×25 ml ether. Residual ether was flushed out with a stream of nitrogen. Dry THF (70 ml) was then added, followed by 11.0 g (0.104 mol) of benzaldehyde. The mixture was stirred mechanically while adding 27.0 g (0.0998 mol) of $CF_3CCl=CHCH_2I$ over 35 minutes with water bath cooling to keep the temperature at 25–30 °C. Stirring was continued for 1 hour. The slurry was filtered and the filtrate treated with 100 ml 2N HCl. The organic layer was separated and the aqueous phase extracted with 100 ml ether. The combined organic layers were washed with water and dried ($Na_2SO_4$). Removal of volatiles at the pump gave 21.6 g of 95% pure product by GC analysis. Distillation provided 18.9 g (76% yield) of the alcohol $PhCH(OH)CCl(CF_3)CH=CH_2$, bp 77° C. at 0.8 mm Hg. $^1H$ NMR (for major diastereomer) δ: 7.3 (Ar); 6.2 (dd, 1H, J=16.7 and 10.8 Hz, C$\underline{H}$=CH$_2$); 5.6 (2H, CH=C$\underline{H}_2$); 5.1 (s, 1H, C$\underline{H}$COH); 2.9 (bs, 1H, OH). $^{19}FNMR$ δ:−71.7ppm.IR (cm$^{-1}$): 3451 (OH); 1645 (weak); 1495; 1410; 1456; 1249; 1188; 1171; 730; 701. Analysis: Calc. for $C_{11}H_{10}ClF_3O$ (250.65): C, 52.71; H, 4.02%. Found: C, 53.09; H, 3.92%.

The alcohol prepared as described above (8.0 g, 31.9 mmol) was stirred with 18 ml 2N NaOH at 85 °C. for 0.5 hour. The cooled reaction mixture was neutralized and the organic product taken up in 25 ml $CH_2Cl_2$, washed with 15 ml water, 15 ml aq. NaCl, dried ($Na_2SO_4$), and distilled at 5 mm Hg to give 4.7 g (22 mmol, 69% yield) of the oxirane, bp 59–63° C. (isomer ratio 10: 1). $^1H$ NMR δ: 7.3 (5H); 5.5 (m, 3H); 4.5 (s, 1H). ). $^{19}F$ NMR δ: −75.5 (s, major isomer); −69.2 (s, minor isomer) ppm. Analysis: Calc. for $C_{11}H_9F_3O$ (214.19): C, 61.68; H, 4.24%. Found: C, 61.63; H, 4.31%.

Example 2

This example illustrates the preparation of 2-trifluoromethyl-2-vinyl-3-isopropyloxirane from $CF_3CCl=CHCH_2I$.

In a manner similar to that used in Example 1, zinc powder was reacted with $CF_3CCl=CHCH_2I$ in the presence of isobutyraldehyde to give $(CH_3)_2CHCH(OH)CCl(CF_3)CH=CH_2$, bp 91° C. at 48 mm Hg. $^{19}F$ NMR: −72.8 ppm (major isomer).

The alcohol so obtained was stirred vigorously with 1.1 equivalents of 1N NaOH at 65–70° C. for 2 hours. The corresponding oxirane, bp 44–48° C. at 55 mm Hg, was obtained in good yield. $^1H$ NMR: 1.0 (dd, 6H), 1.4 (m, 1H), 3.0 (d, 1H), 5.4–6.2 (3H) ppm. $^{19}F$ NMR: −76.3 ppm.

Example 3

This example illustrates the preparation of 2-trifluoromethyl-2-vinyl-3-phenyl oxirane from $CF_3CCl=CHCH_2Cl$.

To a stirred mixture of activated Zn powder (40 g, 0.60 mol), 500 ml anhydrous dimethyl formamide, and 54 ml (0.56 mol) of benzaldehyde, under $N_2$, were added 90 g (0.51 mol) of $CF_3CCl=CH-CH_2Cl$ drop-wise over a period of 60 minutes. The reaction flask was placed in a water bath to moderate the exothermic reaction during the addition of $CF_3CCl=CHCH_2Cl$. After complete addition of $CF_3CCl=CHCH_2Cl$, the reaction mixture was stirred for an additional hour at room temperature and filtered. To the filtrate, 1 liter of 2N HCl and water (500 ml) were sequentially added with stirring. The lower layer was separated, washed with 2% aqueous $NaHSO_3$ (2×100 ml), water (100 ml), dried ($MgSO_4$), and concentrated under reduced pressure to afford 80 g of crude alcohol, which was used in the next step without further purification.

To the crude alcohol obtained above, 125 ml 2N NaOH was added, and the mixture stirred at 85° C. for 45 minutes. The reaction mixture was cooled to room temperature, neutralized with 2N HCl, and the organic material extracted with 300 ml $CH_2Cl_2$. The organic solution was washed with water (2×100 ml), brine (50 ml), dried (MgSO4), and concentrated on a rotary evaporator. Distillation of the resultant material afforded 36.0 g of 2-trifluoromethyl-2-vinyl-3-phenyloxirane.

Example 4

This example illustrates the preparation of 2-trifluoromethyl-2-vinyl-3-phenyl oxirane from $CF_3CCl_2CH=CH_2$.

To a stirred mixture of activated Zn powder (1.3 g, 20 mmol), anhydrous DMF (20 ml), and $C_6H_5CHO$ (2.12 g, 20 mmol) were added $CF_3CCl_2CH=CH_2$ (3.0 g, 17 mmol) drop-wise and the resultant reaction mixture was stirred under a nitrogen atmosphere for 1 hour. Work-up of the reaction mixture, as described in Example 3, afforded 1-phenyl-2-chloro-2-trifluoromethylbut-3-en-1-ol (2.5 g). The crude alcohol was treated with 2N NaOH and worked-up, as described in Example 3, to afford 2.0 g of the corresponding oxirane.

What is claimed is:

1. A compound having the formula:

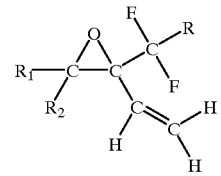

wherein:
R is fluorine, hydrogen, an unsubstituted or substituted aliphatic or unsubstituted or substituted aromatic radical;
$R_1$ is an unsubstituted or substituted aliphatic radical, or unsubstituted or substituted aromatic radical; and
$R_2$ is hydrogen, an unsubstituted or substituted aliphatic radical, or unsubstituted or substituted aromatic radical.

2. The compound of claim 1, wherein:
R is hydrogen, fluorine, an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical;
$R_1$ is an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical;

$R_2$ is hydrogen, an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical.

3. The compound of claim 2, wherein:

R is fluorine, hydrogen, an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl, or an unsubstituted or substituted $C_7$–$C_{11}$ aralkyl, $R_1$ is an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl, or an unsubstituted or substituted $C_7$–$C_{11}$ aralkyl, $R_2$ is hydrogen, an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl, or an unsubstituted or substituted $C_7$–$C_{11}$ aralkyl.

4. The compound of claim 3, wherein R is fluorine or an halongenated $C_1$–$C_3$ alkyl.

5. The compound of claim 4, wherein $R_1$ is a $C_6$–$C_{15}$ aryl selected from the group consisting of phenyl, o-tolyl, m-tolyl, p-tolyl, o-xylyl, m-xylyl, p-xylyl, alpha-naphthyl and beta-naphthyl, and substituted versions of thereof.

6. The compound of claim 5, wherein $R_1$ is a substituted or unsubstituted phenyl, $R_2$ is hydrogen and R is fluorine.

7. The compound of claim 4 wherein $R_1$ is a substituted or unsubstituted $C_1$–$C_5$ alkyl, $R_2$ is hydrogen, and R is fluorine.

8. The compound of claim 4, wherein $R_1$ and $R_2$ are substituted or unsubstituted $C_1$–$C_5$ alkyls, and R is fluorine.

* * * * *